US011458196B2

(12) United States Patent
Pătrașcu (10) Patent No.: US 11,458,196 B2
(45) Date of Patent: Oct. 4, 2022

(54) COMPOSITION, PREPARATION METHOD AND EVALUATION OF A COMPLEX IMMUNOGEN NAMED I-SPGA FOR PRODUCTION OF IMMUNOLOGICAL ACTIVE PROTEINS (IAP)

(71) Applicants: Raul Sorin Fântână, Brașov (RO); Claudiu Adrian Preda, Brașov (RO)

(72) Inventor: Ionel Victor Pătrașcu, Buchare (RO)

(73) Assignees: Raul Sorin Fântâna, Brasov (RO); Claudiu Adrian Preda, Brasov (RO)

( * ) Notice: Subject to any disclaimer, the term of this patent is extended or adjusted under 35 U.S.C. 154(b) by 0 days.

(21) Appl. No.: 16/620,100

(22) PCT Filed: Jun. 5, 2018

(86) PCT No.: PCT/RO2018/000008
§ 371 (c)(1),
(2) Date: Dec. 6, 2019

(87) PCT Pub. No.: WO2019/039948
PCT Pub. Date: Feb. 28, 2019

(65) Prior Publication Data
US 2021/0121552 A1    Apr. 29, 2021

(30) Foreign Application Priority Data
Jun. 6, 2017    (RO) ............................. a 201700340

(51) Int. Cl.
*A61K 39/00*    (2006.01)
*A61K 39/02*    (2006.01)
(Continued)

(52) U.S. Cl.
CPC .......... *A61K 39/02* (2013.01); *A61K 39/0002* (2013.01); *A61K 39/12* (2013.01);
(Continued)

(58) Field of Classification Search
None
See application file for complete search history.

(56) References Cited

U.S. PATENT DOCUMENTS 5,853,765 A    12/1998  Stolle et al.
8,679,504 B2 *  3/2014  Sellers ................... C12Q 1/701
                                                      424/184.1
(Continued)

FOREIGN PATENT DOCUMENTS

CN    104892756    *   9/2015
RO        132299        12/2017
(Continued)

OTHER PUBLICATIONS

Topilescu et al. (Journal of Biotechnology, (Sep. 2014) vol. 185, Supp.SUPPL. 1, pp. S91-S92. "Growth Inhibition of antibiotic resistant bacteria by neurtralizing IgY antibodies" Meeting Info: European Biotechnology Congress 2014. Lecce, Italy. May 15, 2014-May 18, 2014; abstract),.*

(Continued)

*Primary Examiner* — Jennifer E Graser
(74) *Attorney, Agent, or Firm* — Inskeep IP Group, Inc.

(57) ABSTRACT

The present invention relates to the composition and method of preparing an immunogen designated as I-spga consisting of a complex antigen prepared from 18 to 26 species of pathogenic microorganisms isolated from patients, inactivated with binary ethyleneamine (BEI) and formalin, diluted in a SPGA immunopotentiator mixed with QS-21 adjuvant. By inoculating the hens with the I-spga immunogen, hyperimmune eggs (Immunospga) are obtained which contain immunologically active proteins specific to the 18-26 antigens used for immunization. The immune response of the hens is specific to the used antigens by amplification of the antigenic signal by the SPGA immunopotentiator and due to a special immunization program that allows the immune system to act complex and intense: The I-spga complex antigen contains 18-26 microorganisms isolated from patients, bacterial bodies, components from bodies obtained by ultrasonography, cilia, exotoxins, endotoxins, spores, viruses, fungi or yeasts. This pathogenic material is inactivated with BEI and formalin. The I-spga antigen is of three types. The standard I-spga antigen is composed of 18 to 24 antibiotic-resistant bacterial species isolated from patients in Romania. The specific I-spga complex antigen is composed of the I-spga complex antigen containing a mixture of 7-9 strains from a single species of bacteria, fungi or yeasts isolated from patients in Romania mixed with SPGA and QS-21, used for inoculation of hens previously immunized with standard I-spga antigen. The personalized I-spga antigen is composed of patient-derived pathological material containing cellular debris and pathogenic germs inactivated with BEI and formalin and mixed with SPGA and QS-21 and is used to immunize hens previously immunized with the standard I-spga antigen. This now patented technology encompasses a new generation of biological products in which the immune response of the hens to different groups of parenterally inoculated antigens at different time intervals is overlapping. Chicken response is uniform and additional administration of immunogens and SPGA as an immunopotentiator amplifies the antigenic signal and immune response. The I-spga immunogen as well as the immune response contain two markers, G and A, which identify the I-spga antigen used for immunization against the antigens used to produce the Imunoinstant group bio-preparations or similar products. The I-spga immunogen is used to immunize the hens for obtaining immunologically active proteins that can be used to treat immune deficiencies, psoriasis, epidermolysis bullosa, other dermatitises, nosocomial infections, antibiotic-resistant infections in the urinary system of children and grownups.

11 Claims, 2 Drawing Sheets

(51) Int. Cl.
 A61K 39/12 (2006.01)
 C07K 16/02 (2006.01)
 C12Q 1/04 (2006.01)
 G01N 33/68 (2006.01)
(52) U.S. Cl.
 CPC .............. C07K 16/02 (2013.01); C12Q 1/04 (2013.01); G01N 33/6854 (2013.01); *A61K 2039/5252* (2013.01); *A61K 2039/545* (2013.01); *A61K 2039/552* (2013.01); *A61K 2039/55505* (2013.01); *A61K 2039/55516* (2013.01); *A61K 2039/55577* (2013.01); *A61K 2039/70* (2013.01)

(56) References Cited

U.S. PATENT DOCUMENTS

| | | | | |
|---|---|---|---|---|
| 8,859,233 | B2 * | 10/2014 | Larsen | .................. C07K 16/00 435/70.1 |
| 2004/0005327 | A1 | 1/2004 | Subramanian et al. | |

FOREIGN PATENT DOCUMENTS

| WO | WO 2009/027470 A1 | 3/2009 |
|---|---|---|
| WO | WO2016/114677 A1 | 7/2016 |
| WO | WO2016/065626 A1 | 4/2017 |
| WO | WO2017/065626 A1 | 4/2017 |

OTHER PUBLICATIONS

Pătrașcu, I.V. et al., "Biological products PC2. Part 3. Active immunity via passive immunity," *One Health International Journal*, vol. 3, No. 2, May 1, 2017, pp. 116-119, 4 pages.

Pătrașcu, I.V. et al., "Specific activity of immunological active proteins I-spga. The specific reaction against Colistin resistance Klebsiella Pneumoniae strains," *One Health International Journal*, vol. 3, No. 2, May 1, 2017, pp. 120-126, 7 pages.

Bovarnick, M.R. et al., "The influence of certain salts, amino acids, sugars, and proteins on the stability of Rickettsiae," *J. Bacteriol.*, vol. 59, pp. 509-522, 14 pages.

\* cited by examiner

COMPOSITION, PREPARATION METHOD AND EVALUATION OF A COMPLEX IMMUNOGEN NAMED I-SPGA FOR PRODUCTION OF IMMUNOLOGICAL ACTIVE PROTEINS (IAP)

RELATED APPLICATIONS

This application is the U.S. National Phase of and claims priority to International Patent Application No. PCT/RO2018/000008, International Filing Date Jun. 5, 2018, entitled Composition, Preparation Method And Evaluation Of A Complex Immunogen Named I-SPGA For Production Of Immunological Active Proteins (IAP); which claims benefit of Romanian Application No. a201700340 filed Jun. 6, 2017; both of which are incorporated herein by reference in their entireties.

TECHNICAL FIELD

Human medicine, veterinary medicine, immunopathology, polyclonal antibodies, preventive and curative treatments by passive immunization, control of antibiotic resistance.

DESCRIPTION OF THE INVENTION

Presentation of the State of the Art Including Bibliography

During 2012-2014, studies have been conducted concerning the production of the hyperimmune egg and the use of hen immunoglobulins (IgY) These studies have led to several patents (16-20). The above mentioned products were the first generation of immunoglobulins and immunomodulators obtained by a different technology concerning the immunogen used to immunize the hens. The Imunoinstant brand comprise biological products prepared from conventional laying hens in which the polyvalent antigen was prepared from bacteria, yeasts, viruses using for inactivation a standard method with 3% formalin for two hours at 37° C. This method does not allow the preservation of certain antigenic fractions and epitopes present in the antigenic structure of the bacteria, yeasts, viruses or fungi. In all bacterial species, the same method was used, inactivation with formalin and formation of the immunogen with QS-21 adjuvant. There are some bacterial strains for which the ultrasound treatment allows the increase of antigen contact surface. In this generation of biological products the antigenic mass used for immunization, was represented by a mix of antigens obtained from several antibiotic-resistant or -susceptible strains isolated from patients, which, after inactivation, were prepared as immunogen in admixture with QS-21, a purified saponin derivative.

The success of an immunization depends on several factors, including the time intervals between first, second and subsequent immunizations. For this purpose, numerous studies were conducted using 0, 14 and 28 days intervals (37, 26) or once weekly for 7 consecutive weeks (27). Several authors immunize chickens at 10-day intervals (27, 28), but the general recommendation is that the interval between the first and the second injection of the immunogen should be of at least 4 weeks. This reflects the immunological memory, which must be given time to develop (31).

In hens immunized at day 0, week 10 and week 15, very high titres of antibodies were obtained, in the range of 1:160,000 (30). These results were reproducible, were similar, and application of a later impulse was recommended (31, 55). It has been demonstrated that a very high titer can be Obtained by prolonging the pulse interval from 14 to 42 days (32). There is evidence that frequent immunizations over short periods of time lead to immunological depression instead of stimulating the production of antibodies (29).

For preparation of Imunoinstant, the first generation of products, the hens were immunized at short intervals of 10 days, respectively. Instead, in the new generation of biological products which is the subject of this patent, immunization was performed at 0, 30 and 45 days, respectively, leaving time to restore the immunological memory of the hen.

Influence of Immunization on Laying Capacity.

Hen's performance is normally easily influenced by a simple antigen inoculation (40, 34, 35), but the antibody titer may decrease depending on the type of immunogen injected. For example, in hens immunized with solutions containing somatic, secreting-excreting antigens from an intestinal parasite (*Ascaris suum*), the immune response of the inoculated hens decreased or stopped completely after 3 weeks, probably due to the sub-toxic position which originates from para-intestinal sites (35, 36).

In addition, the Freund complete (FCA) and incomplete (FIA) adjuvants influence the stability of antibody (Ab) titers. It was found that the use of FCA caused a significant decrease in the titer of Ab in SPF Rhode Island hens (39), but had only a minor and transient effect (38) or even failed to significantly affect the stability the Ab titre in Leghorn white hens (40). The difference between these results was probably caused by differences in the experimental conditions.

Increase of IgY Titre

After immunization of a rabbit, the immune system produces a primary response followed by a secondary response caused by the injection of the second dose from the same immunogen. The two phases have different characteristics. During the primary response, IgM is synthesized but only at a low and transitory level for raising the antibody titres, while after secondary immunization, IgG antibodies appear at high titers. Antibody titres last for several weeks. IgY antibodies appear in the hen serum approximately 4 days after inoculation of the antigen, reach a maximum titre at 6 to 8 days and decline after that. Ab titre may be increased by booster immunizations. There appear to be two different mechanisms of the secondary immune response According to the results, some chickens respond with mammalian-like antibody kinetics, while others respond to the same immunization protocol with an increase in the Ab titer after the first immunization, but fail to make significant changes after the second inoculation.

Most frequently, the antibody titer kinetics in hens after the first immunization show a transient IgY increase in the first phase, while the second phase (booster immunization) is characterized by an initial increase in the Ab titer for approximately 10 days, followed by a plateau for another 10 days and a drop after that Increase of antibody titre is probably a consequence of the relatively short half-life of IgY as compared to IgG. On the contrary, some authors have shown that the Ab titres remain high and stable for several weeks (41, 42, 43, 44). Until now, the reasons for these differences in the kinetics of antibody production remain unclear.

To increase the antibody titer, the solution presented in this patent, will relay on new formulations for immunopotentiators (SPGA) and adjuvants (QS-21), and will use a modified immunization program.

Imunoinstant products (16-19) have not been grouped according to their medical intended use (oral, cutaneous, mucosal, respiratory), nor was a program set up to control and differentiate these products.

No immunopotentiators have been used to increase the antigenicity in direct relationship with the immune system of the immunized hen and no immunopotentiator was used as final diluent For this immunogen, in combination with QS-21. Tween 20 was used as an emulsifier to increase superficial tension on the antigenic proteins (16, 19).

Our studies in IMUNONOMEDICA-SH laboratories aimed at improving the preparation conditions of the immunogens, in respect to antigenic content, complexity of antigens, selective inactivation, use of immunopotentiator and Tween 20 as an emulsifier Preclinical and clinical studies on humans support the need for preventive and curative use of immunologically active proteins (IAP) as well as other products containing immunomodulators, contact proteins, peptides and radicals present in the hyperimmune egg. Concerns about the hyperimun egg, as set forth in this patent, have been aimed at improving the quality of immunogens prepared from bacteria, yeasts and viruses and increasing their immunogenicity. To this purpose, the use of binary ethyleneimine (BEI) and formalin as inactivatants, the fragmentation of bacterial bodies by ultrasonography and gamma radiation inactivation were tested.

The antigenic stimulus was amplified by the use of a SPGA immunopotentiator, studied by the author since 1970 and used in the production of vaccines after 1972. SPGA has been shown to have protective activity on herpes viruses (cell-free) extracted from infected cells (cell-associated), as well as potentiator of antigenic stimulus in the body of the immunized hens (1-8). SPGA is used in the production of new immunogens for humans and animals (6-9).

We shall continue to use hens for immunization and hyperimmune eggs from which immunological active proteins (IAP) will be extracted. Antibody response in hens (Gallus domesticus) is more pronounced due to a longer phylogenetic distance between it and the product used for immunization. This phenomenon also refers to the relationship between IAP prepared from the hyperimmune egg and humans, as organisms that come into contact with the IAP. The accessibility of IAP in the human body is due to oral or on other mucosae administration and to the ancestral relationships between birds and humans. Mammals and birds have a common ancestor with an evolutionary drift of 350 million years inbetween. For this reason, it is possible that IAPs to be recognized as self in the human body.

The diversity of hen antibodies is mainly achieved by gene conversion and, additionally, addition, by the V-J flexibility play and the somatic point mutations as in mammals. In contrast to mammals, there is only one VH or VL gene in chickens, but in addition there are about 25 so-called pseudo-V-genes (which have lost the usual sequences for transcription regulation and signal recognition). Hens can frequently produce antibodies that will recognize more epitopes than mammalian antibodies (9-11). In these immune processes, by administering immunologically active proteins, the network of lymphocytes and molecules possessing variable regions (V) is invoked. The immune system is therefore seen as a network with components interconnected by V-V interactions. The T helper and suppressor cells, the role of accessory cells in non specific immune responses (74-78).

The use of glutamate, which acts on hen's T lymphocytes, increases the antigenic signal and Makes the mature lymphocyte to take it over, store and transfer it from its V variable onto the variable V of hyperactive B lymphocyte, which will start the production of immunoglobulins with higher affinity to the antigens that originally produced the information.

Until this date, sodium glutamate has not been used as an immunomodulator in the immunogen prepared from 18-26 antigens from bacteria, viruses, fungi or yeasts. Recent studies have shown that glutamate is not only a neurotransmitter, but has also an important immunomodulator role. In this regard, several glutamate receptors have recently been described on the surface of T cells, while glutamate transporters have been expressed in antigen presenting cells, such as dendritic cells and macrophages. This opinion integrates and summarizes the various findings in this emerging field. It is necessary to study the role of glutamate as a key immunomodulator in initialing and developing the immunity of T cells mediated in peripheral tissues as well as in the central nervous system (13).

The immunogen called I-spga is of three types: standard, specific and custom. Using this type of immunogen, a stronger immune response is obtained in the immunized hen and the antibodies exhibit a higher reaction capacity. These IgY antibodies are present in the yolk and the vitelline membrane. In the egg white, active immunological proteins are present, such as apo and holo ovotransferrin, ovomucine, ovalbumin and lysozyme. Besides egg white, these products are also found in the cochlear membrane and in the egg shell still attached to the shell membrane. These immunologically active proteins potentiate immunologically the whole hyperimmune egg, allowing a diversification of the derived biological products as well as the forms of treatment.

REFERENCES

1. Bavarnick, M. R., J. C. Miller, and J. C. Snyder. 1950. The influence of certain salts, amino acids, sugars, and proteins on the stability of Richettsiae. J. Bacteriol. 59:509-522.
2. Calnek B. W. Hitchner S. B., and Adlinger H. K. Lyophilization of Cell-Free Marek's Disease Herpesvirus and a Herpesvirus from Turkeys. Applies Microbiology, Vol. 20, November 1970, p. 723-726
3. BREVET. Procedeu de preparare a vaccinului contra bolii lui Marek dintr-o tulpina de virus herpes de eurea. Brevet nr. 56778 din Jun. 27, 1973. Patrascu I. V.
4. Vaccin inactivat contra leucoze ienzootice bovine Și ovine si procedeu de preparare a lui. Brevet nr. 75101 din Aug. 10, 1980. Patrascu I. V., Stube P, Sofia Coman, Sandu I., Maria Ciobanu.
5. Brevet. Procedeu de preparare a vaccinului contra bolii lui Marek. (Completare la Brevet nr. 56778). Nr 80570 din Oct. 14, 1982. Patrascu I. V
6. Patrascu, I. V., Calnek B. W., and Smith M. W. HVT vaccine and challenged with virulent Marek's disease virus. Avian Dis. 17:137-141. 1973.
7. Patrascu I. V., Calnek B. W. In vitro assay of cell-free turkey herpesvirus (1972). Avian Diseases vol. 16. nr.2. p:357-419
8. Patrascu I. V. Tuschak N., Elena Tuschak, Stiube P., Niteanu V., Popa V., Mihailescu D. Marek's disease and its control in the Socialist Republic of Romania. Acta Vet. Bruno 43.1974. p:171-182.
9. R. Schadeet al., Chicken Egg Yolk Antibodies, Production and Application. 2000, Springer-Verlag, Lab Manuals, ISBN 3-540-66679-6. Video tutorial of IgY purification.
10. Xu Y, Li X, Jin L, Zhen Y, Lu Y, Li S, You J, Wang L Application of chicken egg yolk immunoglobulins in the control of terrestrial and aquatic animal diseases: a review. Biotechnol Adv. 2011 November-December; 29(6):860-8. Epub 2011 Jul. 20.
11. Dávalos-Pantoja and Hidalgo-Alvarez, Colloidal stability of IgG- and IgY-coated latex microspheres, 2001.
12. Institutul National de Cercetare-Dezvoltare pentru Microbiologie Ş i Imunologie "Cantacuzino". Imunostimulent BCG liofilizat.
13. Rodrigo Pacheco, Teresa Gallart, Carmen Lluis, Rafael Franco. Role of glutamate on T-cell mediated immunity. Neuroimmunogloy. April 2007, Volume 185, Issues 1-2, Pages 9-19.
14. Patrascu I. V., Chiurciu C., Viorica Chiurciu, Sima Lucica, Mihai Iuliana, Violeta Ionescu, Ioana Dimulescu, Dana Tiplea, Cristina Casaru, Andreia Dinu, Georgiana Topilescu, Georgiana Radu, Angelescu C. ISBN 978-973-0-2282-9. Psoriarzisul privit dintr-un alt punct de vedere. Bucuresti 2016
15. Bahnemann H G. Binary ethylenimine as an inactivant for foot-and-mouth disease virus and its application for vaccine production. Arch Viva 1975; 47(1):47-56
16. Patent (CBI) nr. A/00156 din Feb. 25, 2014—"Procedeu de obtinere ş i utilizare a imunoglobulinelor de gâinâ (IgY)," Pâtraş cu Ionel Victor, Viorica Chiurciu, Chiurciu Constantin, Georgiana Topilescu.
17. Patent (CBI) nr. A/00179 din Mar. 5, 2014 "Metode de evaluare imunplogicâ a activitâtii specifice a imunoglobulinelor de pasâre (IgY)" Pâtraş cu Ionel Victor, Viorica Chiurciu, Chiurciu Constantin, Georgiana Topilescu.
18. Patent nr.A/00653 din Aug. 28, 2014—"Producerea ş i utilizarea ovotransferinelor moderne (OTF-M)" Pâtraş cu Ionel Victor, Viorica Chiurciu, Chiurciu Constantin, Manana Oporanu, Georgiana Topilescu.
19. Patent (CBI) nr. A/00810 din Oct. 29, 2014 "Producerea ş i folosirea oului hiperimun PC2" Pâtraş cu Ionel Victor, Viorica Chiurciu, Chiurciu Constantin, Mariana Oporanu, Georgiana Topilescu, Iuliana Mihai.
20. Patent (CBI) nr. A/00008/Jan. 13, 2015—Producerea si utilizarea ovotransferinei PC2 (OTf-PC2) Patrascu I. V., Viorica Chiurciu, Chiurciu C, Mariana Oporanu, Georgiana Topilescu si Iuliana Mihai.
21. USA CA 2775564A1 Shibo Jiang, Lanyng Du. Immunopotentiator-linked oligomeric influenza immunogenic compositions. 2016
22. US 20160296617 A1, Shibo Jiang, Lanying Du, Yusen Zhou, Guangyu Zhao. Immunogenic Composition for MERS Coronavirus Infection
23. WO 2006113372 A2, John Ellis, Catherine Charreyre, Olivier Michel Martinon, Porcine circovirus and *helicobacter* combination vaccines
24. CA 2187974 C. Carla Christina Schrier, Heinrich Dieter Lutticken. Newcastle disease virus combination vaccine
25. U.S. Pat. No. 6,558,678 B1. Jan Holmgren, Ann-Mari Svennerholm. Preparation and use of formalin-killed colonization-factor-antigen (cfa)-expressing *E. coli* organisms for vaccination against enteric infection/diarrhea caused by enterotoxigenic *E. coli* bacteria in humans.
26. Calzado, E. G., Marino, E. C., Chavez, T. S., Vazquez, E. L., Ochoa, Z. C. & Schade, R. (2003). Extraction of a monospecific Coombs-reagent from chicken eggs. ALTEX 20, 21-25.
27. Ohnishi, T., Kakimoto, K, Hashida, S., Fujii, M., Hirono, S., Nishiayma, K, Amita, Y., Ishikawa, E., Tsubouchi, H. & Daikuhara, Y. (2000). Development of highly sensitive enzyme-linked immunosorbent assays for hepatocyte growth factor/scatter factor (HGF/SF): determination of HGF/SF in serum and urine from normal human subjects. Journal of Immunological Methods 244, 163-173.
28. Pelosi, E., Lambden, P. R., Caul, E. O., Liu, B., Dingle, K., Deng, Y. & Clarke, I. N. (1999). The seroepidemiology of genogroup 1 and genogroup 2 Norwalk-like Viruses in Italy. Journal of Medical Virology 58, 93-99.
29. Gassmann, M., Weiser, T., Thömmes, P. & Hübscher, U. (1990). Das Hühnerei als Lieferant polyklonaler Antikörper. Schweizer Archiv für Tierheilkunde 132, 289-294.
30. Messerschmid, S. & Sarkar, S. (1993). Raising polyclonal antibodies against TMV in a hen utilizing the immunological memory (in German). Anzeiger für Schädlingskunde, Pflanzenschutz, Umwelt-schutz 66, 145-147.
31. Hlinak, A., Schrödl, W., Witt, S., Schade, R. & Krüger, M. (1996). Production of egg yolk antibodies against human cell-associated antigens. ALTEX 13, Suppl. 1, 76-79.
32. Janeway, C. A., Travers, P., Walport, M. & Shlomchik, M. (2002) Immunologie, 5th ed., 777pp. Heidelberg & Berlin, Germany: Spektrum Akademischer Verlag.
33. Pichler, H. (1999). Development of an Enzyme-immunoassay for the Determination of the Mycotoxin Zearalenone Based on Egg-yolk Antibodies from Immunized chickens. Doctoral Thesis. 119pp. Vienna, Austria: Technical University of Vienna
34. Mittermeier, P. (1995). Das Lipopeptid Pam3Cys-Ser-(Lys)4-eine Alternative zu Freundschem komplettem Adjuvans (FCA) bei der Immunisierung von Legehennen zur Gewinnung von Dotterantikörpem. Inaugural Dissertation, Tierärztliche Fakultät der Ludwig Maximilians Universität. 99 pp. Munich, Germany: Ludwig Maximilians University.
35. Schade, R., Bürger, W., Schönberg, T., Schniering, A., Schwarzkopf, C., Hlinak, A. & Kobilke, H. (1994). Avian egg yolk antibodies: the egg laying capacity of hens following immunization with antigens of different kind and origin and the efficiency of egg yolk antibodies in comparison to mammalian antibodies. ALTEX 2, 75-84.
36. Schniering, A., Schade, R. & Hiepe, T. (1996).Development of an IgY-based assay for the detection of *Ascaris suum* antigens. ALTEX 13, Suppl. 1, 62-65.
37. Tini, M., Jewell, U. R., Camenisch, G., Chilov, D. & Gassman, M. (2002). Generation and application of chicken egg-yolk antibodies. Comparative Biochemistry and Physiology—A Molecular and Integrative Physiology 131, 569-574.
38. Mittermeier, P. (1995). Das Lipopeptid Pam3Cys-Ser-(Lys)4-eine Alternative zu Freundschem komplettem Adjuvans (FCA) bei der Immunisierung von Legehennen zur Gewinnung von Dotterantikörpem. Inaugural Dissertation, Tierärztliche Fakultät der Ludwig Maximilians Universität. 99 pp. Munich, Germany: Ludwig Maximilians University.
39. Bollen, L. S. & Hau, J. (1999). Freund's complete adjuvant has a negative impact on egg laying frequency in immunised chickens. in Vivo 13, 107-108.
40. Hlinak, A. & Schade, R. (2000). Possibilities of keeping laying-hens to obtain antibodies. in Chicken Egg Yolk Antibodies, Production and Application: IgY Technology (ed. R. Schade, 1. Behr, M. Erhard, A. Hlinak & C. Staak), pp. 9-24. Berlin, Germany, Heidelberg, Germany, & New York, N.Y., USA: Springer Lab Manuals.
41. Hlinak, A., Schade, R., Bartels, T. & Ebner, D. (1996). Das Huhn als Versuchstier und Quelle spezifischer Dotterantikörper. Erfahrungen zur Haltung, Immunisierung und Legeleistung. TierärztlicheUmschau 51, 402-408.

42. Hommel, U. & Behn, I. (2000). Einsatz aviärer vitelliner Antikörper als Sekundärreagenzien in immunologischen Testsystemen. in Forschung ohne Tierversuche (ed. H. Schöffl, H. Spielmann, F. P. Gruber, H. Appl, F. Harrer, W. Pfaller & H. A. Tritthart), pp. 263-268. Vienna, Austria, New York, USA: Springer.

43. Hatta, H., Tsuda, K., Akachi, S., Kim, M. & Yamamoto, T. (1993). Productivity and some properties of egg yolk antibody (IgY) against human rotavirus compared with rabbit IgG. Bioscience, Biotechnology and Biochemistry 57, 450-454.

44. Behn, I., Hommel, U., Oertel, M. & Hauschild, S. (1969). Kinetics of IgY formation after immunisation of hens with different protein antigens. ALTEX 13, Suppl. 1, 18-21.

45. Seqvential separation of lysozyme; ovomucin, ovotransferrin and ovoalbumin from egg white—Abeyrathne E D, Lee H Y, Ahn D U—Poult Sci. 2014 April. 93(4): 1001-9.

46. Stadelman W. J., Cotterill O. J. 4th ed. Westport, Conn.: AVI Publ. Co.; 2001. Egg Science and Technology.

47. Huopalahti R, Fandino R. L., Anton M., Schade R. Bioactive Egg Compounds. New York, N.Y.: Springer; 2007. Egg White Compounds. Subpart 1b; p. 33-66.

48. Nisbet A. D., Saundry R. H., Moir A. J. G., Fothergill L. A., Fothergill J. E. The complete amino-acid sequence of hen ovalbumin. Eur. J. Biochem. 1981; 115:335-345.

49. Huntington J. A., Stein P. E. Structure and properties of ovalbumin. J. Chromatogr. B Biomed. Sci. Appl. 2001; 756:189-198.

50. Datta D., Bhattacharjee S., Nath A., Das R., Bhattacharjee C., Datta S. Separation of ovalbumin from chicken egg white using two-stage ultrafiltration technique. Separ. Purif. Tech. 2009; 66:353-361.

51. Hopkins F. G. On the separation of a pure albumin from egg white. J. Physiol. 1900; 25:306-330.

52. Chick H., Martin C. J. The precipitation of egg albumin by ammonium sulfate. A contribution to the theory of the "Salting Out" of proteins. Biochem. J. 1913; 7:380-398.

53. Desert C., Dubiard C. G., Nau F., Jan G., Val F., Mallard J. Comparison of different electrophoretic separations of hen egg white proteins. J. Agric. Food Chem. 2001; 49:4553-4561.

54. Ward T. M., Edwards R. A., Tanner R. D. Separating a mixture of egg yolk and egg white using foam fractionation. Appl. Biochem. Biotechnol. 2007; 137-140:927-934.

55. Awade A. C., Efstahiou T. Comparison of three liquid chromatography methods for egg-white protein analysis. J. Chromatogr. B Analyt. Technol. Biomed. Life Sci. 1999; 723:69-74.

56. Williams J. A comparison of glycopeptides from the ovotransferrin and serum transferrin of the hen. Biochem. J. 1968; 108:57-67.

57. Wu J., Acer-Lopez A. Ovotransferrin: Structure, bioactivities and preparation. Food Res. Int. 2012; 46:480-487.

58. Ko K. Y., Mendonca A. F., Ahn D. U. Effect of ethylenediaminetetraacetate and lysozyme on the antimicrobial activity of ovotransferrin against *Listeria monocytogenes*. Poult. Sci. 2009; 87:1649-1658.

59. Fraenkel-Conrat H., Feeney R. The metal-binding activity of conalbumin. Arch. Biochem. 1950; 29:101-113.

60. Valenti P., Antonini G., Fanelli M. R. R., Orsi N., Antonini E. Antibacterial activity of matrix-bound ovotransferrin. Antimicrob. Agents Chemother. 1982; 21:840-841

61. Ibrahim H. R., Sugmito Y., Akoi T. Ovotransferrin antimicrobial peptide (OTAP-92) kills bacteria through a membrane damage mechanism. Biochim. Biophys. Acta 2000; 1523:196-205.

62. Tankrathok A., Daduang S., Patramanon R., Arakai T., Thammasirirak S. Purification process for the preparation and characterization of hen egg white ovalbumin, lysozyme, ovotransferrin and ovomucoid. Prep. Biochem. Biotechnol. 2009; 39:380-399.

63. Radziejewska R. C., Leśnierowski G., Kijowski J. Properties and application of egg white lysozyme and its modified preparations—A review. Polish J. Food Nutr. Sci. 2008; 58:5-10.

64. Alderton, M., Ward W. H., Fevold H. L. Isolation of lysozyme from egg white. J. Biol. Chem. 1945; 157:43-58.

65. Safarik I., Sabatkova Z., Oldrich T., Safarikov M. Magnetic cation exchange isolation of lysozyme from native hen egg white. Food Technol. Biotechnol. 2007; 45:355-359.

66. Chang H. M., Yang C. C., Chang Y. C. Rapid separation of lysozyme from chicken egg white by reductants and thermal treatment. J. Agric. Food Chem 2000; 48:161-164.

67. Wang J., Wu J. Effect of operating conditions on the extraction of ovomucin. Process Biochem. 2012; 47:94-98.

68. Durance T. D. Egg Uses and Processing Technologies, New Developments. CAB Int. Wallingford, UK; 1994. Separation, purification and thermal stability of lysozyme and avidin from chicken egg white; p. 77-93.

69. MORTON, D. M. Requirements for the toxicological testing of drugs in the USA, Canada and Japan. In: GORROD, J. W. (Ed.). Testing for toxicity. London: Taylor & Francis, 1981. p.11-19.

70. MORTON, D. M. Importance of species selection in drug toxicity testing. Toxicol. Lett, v.102, p.545-550, 1998.]

71. SWANSTON, D. W. Assessment of the validity of animal techniques in. eye-irritation. testing. Food Chem. Toxicol. v.23, p.169-173, 1985

72. Evonuk K S et al. Inhibition of System Xc(−) Transporter Attenuates Autoimmune Inflammatory Demyelination. J Immunol 195:450-63 (2015).

73. Sloniecka M et al. Expression Profiles of Neuropeptides, Neurotransmitters, and Their Receptors in Human Keratocytes in Vitro and in Situ. PLoS One 10:e0134157 (2015). Functional 74. N. K. Jerne (1974). Towards a network theory of the immune system. Ann. Immunol. (Inst. Pasteur), 125C, 373-389

75. Shellam G. R., Nossal G. J. V. (1968). "The mechanism of induction of immunological paralysis. IV. The effects of ultra-low doses of flagellin". Immunology 14 (2): 273-284. PMC 1409291.PMID 5640947.

76. Claman Chaperon, Triplett R. F. (1966). "Immunocompetence of transferred thymus-marrow cell combinations". J. Immunol. 97: 928-832.

77. Tada T., Takemori T. (1974). "Selective roles of thymus-derived lymphocytes in the antibody response. I. Differential suppressive effect of carrier-primed T cells on hapten-specific IgM and IgG antibody responses". J. Exp. Med. 140 (1): 239-252.

78. Evans R, Grant C. K., Cox H., Steel K, Alexander P. (1972). "Thymus-derived lymphocytes produce an immunologically specific macrophage-arming factor". J. Exp. Med. 136 (5): 1318-1322

SUMMARY OF THE INVENTION

Brief Formulation of the Technical Solutions
The Objective

To develop a technology for preparation of immunogens that preserve the antigenic structures as close to the original structures as possible, which will generate a complex immune response, an immune response against several epitopes, with increased antibody coupling power including validity, amplification of the avidity of immunologically active proteins, increasing the combination between affinity and avidity.

The I-spga immunogen inoculated in Rhode Island Red or Leghorn or SPF laying hens produces an adequate immune response for a period of over 40 weeks. The specific immune response is equal for each antigen, among a complex of up to 24 antigens. Each antigen is a blend of at least 7 strains of the same microorganism species, all germs being isolated from patients in Romania during 2016-2017. The immunogen administrated to hens should have the ability to form biologically active molecules at a pre-embryonic stage. These protein molecules from the egg have not been recognized in the literature and have not been studied until this technology has been applied.

All the immunologically active molecules such as ovalbumin, ovotransferrin, apo and holo forms, lysozyme and ovomucine, react immunologically specific for each of the antigens with which the hen was immunized, similar to IgY.

The immunogen called I-spga can be identified by two markers, G and A, using the techniques mentioned in this patent. No other similar product, at this date, uses biological markers for identification.

Following preclinical and clinical studies in hens and humans which responded to several technical and therapeutic needs, the following were obtained:

1. The I-spga standard immunogen comprising antigens prepared from 18-26 types of pathogens isolated from patients. I-spga is used to immunize hens which will lay standard hyperimmune eggs that are used in the production of immunologically active proteins (IAP).
2. The specific I-spga immunogen which consists of an antigen prepared from at least seven strains of the same species of bacteria or yeasts. This S-antigen is prepared in admixture with SPGA as immunopotentiator and QS 21 as adjuvant. It is used to reimmunize hens which were immunized with the standard immunogen. Finally, a complex immune response, consisting of the standard and the specific immune response, is obtained. It is recommended for the treatment of *Clostridium difficile* infections, candidosis, etc.
3. The personalized/custom I-spga immunogen prepared from the pathological material collected from a patient, which is mixed with SPGA as immunopotentiator and QS-21 as adjuvant. This P-immunogen is inoculated into hens already immunized with the standard immunogen.
4. Standard hyperimmune eggs originating from hens inoculated with the standard immunogen and used for the treatment of immune deficiencies, including psoriasis and epidermolysis bullosa, in prevention and control of nosocomial infections, etc.
5. Specific hyperimmune eggs originating from hens inoculated initially with the standard immunogen and, after minimum 30 days, inoculated with the S-immunogen.
6. Personalized/Custom hyperimmune eggs originating from hefts inoculated initially with the standard immunogen and, after minimum 30 days, inoculated with the P-immunogen.

The I-spga immunogen contains a complex antigen whose composition depends on the purpose for which the I-spga hyperimune egg is prepared.

The standard antigen contains a blend Of 18-26 Antigens prepared from whole bacteria and/or yeasts, fractions of bacteria or yeasts obtained by ultrasonography, viruses and fungi. Bacterial and yeast antigens are in turn a blend of at least 7 antibiotic-resistant or -susceptible bacterial strains, and 5-7 yeast strains isolated from patients, resistant or susceptible to antibiotics.

The specific antigen is a component that is administered supplementary and consists of 5-7 bacterial strains representative for each species of interest. This antigen, prepared as immunogen, is inoculated 30-40 days after the immunization of the hens with the standard immunogen.

The custom antigen is made up of cell debris and microbial content collected as pathological material from a patient, from infected wounds, from psoriatic plaques, from mucous membranes or from urine. The bacteria isolated from the pathological material are cultivated in the laboratory, identified and inactivated, forming part of the customized antigenic content. The immunogen for inoculation is obtained by addition of SPGA and QS-21, and will be injected to standard immunized hens, at 30-40 days after the primary immunization.

The standard, specific, and customized immunogens are a microbial antigen mixture, 20 mg of each, diluted in 0.5 ml SPGA and 0.5 ml QS-21, respectively, for each hen.

The standard immunogen is administered to Rhode Island Red, Leghorn conventional or SPF hens, aged 18-20 weeks, 2 ml immunogen by intramuscular route. Immunization is repeated after 30 and 44 days, respectively.

Control of the immune response is performed 8 days after the first inoculation on blood samples, by quantitative and qualitative assessment of immunoglobulins, using ELISA and rapid and slow seroagglutination tests.

The supplementar immunization with monospecific or custom antigens is done by the same procedure.

Upon controls at days 30, 44, and 68, respectively, the total number of immune-responsive hens is determined, as well as the specificity of the immune response. At 68 days after the first immunization, quantitative and qualitative controls for all antigens used for immunization are also performed.

To control the immune response after the first immunization, IgY is extracted and tested qualitatively and quantitatively using ELISA and rapid seroagglutination and slow seroagglutination.

The immunogen is stored at +4° C. and tested for the specific immune response in the inoculated hens at 8, 44 and 58 days after the first inoculation.

The immunization program is valid and the I-spga hyperimmune eggs can be used in production if the immune response is uniform in all inoculated birds and the amount of IgY is at least 300 mg/egg.

In the case of custom I-spga production, the eggs may be used even 8 days after the inoculation of the custom immunogen, if the immune response is positive, specific and in the I-spga-P hyperimmune egg contains at least 200 mg of IgY.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DETAILED DESCRIPTION OF THE INVENTION

Obtaining the Standard, Specific and Personalized I-SPGA Immunogen

The standard immunogen. The standard I-spga biological product is prepared from 20-24 microbial antigens used for immunization of the laying hens. The antigen is represented by bacteria and yeasts isolated from hospitalized patients between 2016 and 2017. This product is used for immunization of the hens which will produce the standard hyperimmune eggs.

The specific I-spga immunogen. To the immunogen prepared from 16-20 germs, an immunogen specific to a certain bacterial of yeast species is added, inactivated Under the same conditions, with binary ethyleneimine (BEI) and formalin. This specific immunogen is added to the standard immunogen or is used to additionally immunize birds already immunized With the standard I-Spga (containing 16-20 types of antigens in its structure).

The personalized I-spga immunogen is obtained from a pathological material collected from a patient whose treatment with the standard I-spga immunogen was not successful, which is inactivated with BEI and formalin and, after purification, mixed with SPGA, QS-21 adjuvant and Tween 20. This immunogen is blended with the standard immunogen and the mixture used to immunize a new lot of hens, or is used by itself to immunize already standard immunized hens. In accordance with the present invention, the preparation of the standard I-spga, specific I-spga and custom I-spga Immunogens comprises several steps, among which: preparation of the antigens, preparation and control of I-spga immunogens.

Preparation of the Antigen

In accordance with the present invention, 18-26 antigens are prepared from different pathogenic germs isolated from patients. The bacterial and yeast strains used for this purpose may be susceptible or resistant to antibiotics. These strains are part of the laboratory collection and originate from hospitals in Bucharest or from patients who requested treatment in the IMUNOMEDICA-SH medical clinic: For the control of the strains isolated from patients, strains from international collectionsare are used, officially purchased, with quality certificates and scientific guarantees.

For the specific I-spga, an S-antigen is designes for each microorganism, which contains the most representative and most commonly encountered species/strains in patients as subtypes. For example, for *Staphylococcus* spp., the blend consists of *S. aureus, S. lugdunensis, S. haemolyticus, S. warneri, S. schleiferi, S. intermedius, S. saprophyticus*. The choice of bacterial strains or yeasts is in line with international standards, but they come from patients in Romania. The structure of an I-spga immunogen includes: *Escherichia coli, Staphylococcus aureus, Fusobacterium nucleatum, Staphylococcus epidermidis, Enterococcus* spp., *Enterococcus faecium, Enterococcus faecalis, Corynebacterium* spp., *Corynebacterium diphteriae, Klebsiella* spp, *Klebsiella pneumoniae, Proteus mirabilis, Proteus* spp., *Candida glabrata, Candida albicans, Streptococcus pneumoniae; Salmonella enteritidis, Salmonella typhimurium, Acinetobacter baumani; Clostridium difficile* vegetative form; *Clostridium difficile* sporulated form, *Clostridium difficile* exotoxins A and B, *Pseudomonas aeruginosa, Neisseria meningitidis, Haemophilis influenzae, Helicobacter pylori,* the composition depending on the frequency of infections with antibiotic resistant germs or being demand. For the custom I-spga, a P-antigen is assembled consisting of cellular debris and the pathogenic group of pathogens opresent in psoriatic plaques, other wounds without scarring tendency, or pathological products collected from mucosae, sputum, and/or urine. The bacterial cells, cultivated and identified, are washed 3 times in phosphate buffer (PBS) and centrifuged at 4000 rpm for 15 minutes at 20° C., inactivated with either BEI or formalin or gamma radiation and freeze-dried in 10 ml vials, 4 ml of bacterial suspension in each vial. After lyophilization, the vials are stored at −20° C. 50 mg of bacterial bodies are resuspended in phosphate buffer (PBS) at the concentration represented by an optical density $OD_{600}=1.00$ and mixed with 45 µl QS-21 adjuvant.

Preparation of Immunogenes

Immunization is the most important step in the production program of the immunologically active proteins, when in the body of the inoculated hens, a complex antigenic stimulus is developed which allows the transfer of the antigenic information to the V variable of immature T lymphocyte V which subsequently, by transformation form naive lymphocyte into mature lymphocyte; stores the information in its DNA and starts to clonate immediately. The mature T-lymphocyte transfers the information about the structure of antigens to the B lymphocyte, which, in turn; produces immunoglobulins. These immunoglobulins are transferred into the yolk which finally is integrated into the egg.

The only places in the egg where the immunoglobulins are found (IgY) is the yolk and the vitelline membrane. In the white, the shell membrane and the egg shell no IgY was found (Pâtraş cur I. V. unpublished data).

Inactivation of pathogenic germs is performed differently, depending on each microorganism, with formaldehyde, or bromoethylamine-2-bromohydrate (BEA) and sodium thiosulfate; purchased from Sigma-Aldrich. The used inactivation methods are:

Inactivation with Formalin and Binary Ethyleneimine (BEI)

This method of inactivation is used for various bacteria including *Clostridium difficile*, vegetative form and spores. This test is based on a kinetic inactivation assessment. Under optimal conditions, BEI inactivation rates are 0.5-1.0 $\log_{10}$ per hour. Generally, final inactivation occurs after 48 hours. Formaldehyde, the "classic" inactivation agent, inactivates bacteria at a rate of only 0.3 $\log_{10}$ per hour. In our used inactivation program, formalin is added at the start of the inactivation process as soon as BEI was added to the bacterial suspension. Under these conditions, the rate Of inactivation is higher than 2-3.5 $\log_{10}$ per hour. This procedure allows inactivation overnight at high levels of protection of the antigens. It is known that formaldehyde also makes cross-links between the proteins present in the inactivated material, stabilizing thus the antigen (15). Following inactivation, the suspension was stored at 4° C. and a representative sample was taken and tested for completion of inactivation. If inactivation was complete, the antigenic mass was separated by centrifugation at 4000-6000 rpm, excess formaldehyde removed by tangential filtration and the antigen resuspended in SPGA to a concentration of 20 mg protein/ml. Afterwards the antigen is suspended in SPGA and mixed with the QS-21 adjuvant. The immunogen is stored at 4° C. until use.

BEI was prepared by cyclization of 0.1 M bromoethylamine hydrobromide (BEA) (Sigma) in 0.1 M NaOH 5 M solution for one hour at room temperature according to the Bahnemann method (13). Cyclization of 0.1 M BEA in active form was confirmed by BEI, by changing the pH front 12 to 8. The solution was freshly prepared before each experiment. Controls of inactivation with BEI were performed using formaldehyde as inactivation control and an untreated culture as negative control.

BEI Virus Inactivation

The Flury rabies virus and CVS suspension are inactivated with BEI 6 hours at 37° C., under constant shaking and pH correction to 7.6. After inactivation, BEI is neutralized with BEA.

Mixing the Antigen with SPGA as Immunopotentiator

Bacterial and levurian antigens, standard, specific or custom preparations, stored at 4° C., after confirmation of inactivation, arc centrifuged at 4000 rpm for 30 minutes, and the sediment resuspended in SPGA and homogenized at room temperature for 30 minutes by shaking.

Mixing the Antigen with SPGA and QS-21 Adjuvant

Over the antigen and SPGA mixture, add the same volume of 0.2% diluted QS-21 adjuvant and shake for 15 minutes to homogenize. Transfer to sterile storage containers and store at +4° C. until use.

Use of I-SPGA Products for the Immunization of Laying Hens and Control of Immunization Immunization of Conventional or SPF Laying Hens The immunization of laying hens with the selected antigen is well known technique. The present invention may employ any method for immunization of hens which allows administration of the given antigen by any route: intramuscular, subcutaneous, intracutaneous, intramuscular, intravenous.

For immunization and immunization control, conventional Rhode laying or Leghorn white or SPF laying hens, aged 18-20 weeks, are used. The standard, specific or personalized I-spga is administered by intramuscular route, 2 ml per hen, 0.5 ml in four different points of the chest muscles. Immunization of the hens is continued and I-spga administration is repeated 30 and 44 days, respectively, after the first inoculation.

The immune response is controlled directly from the hyperimmune egg or serum. The control is performed at 8, 30 and 44 days, respectively, after the first inoculation. The final control is done 14 days after the last immunization and periodically throughout the use period of the immunized hens.

From the eggs harvested for control, IgY is extracted by the simplified method, at cold. For this purpose, the yolk is separated and processed individually by cold extraction of IgY in deionized water acidified with 0.1N HCl, pH 5.1, at a 1:8 ratio, and overnight incubation at +4° C. IgY is separated from the water by centrifugation at 4000 rpm for 15 minutes. The supernatant, which contains the pH 5.1 water-extracted immunoglobulins, can be preserved by freezing in 1 ml cryotubes at −20° C. or −85° C. For routine control activities it is recommended to use thimerosal to limit bacterial multiplication. Thimerosal is better than azide because azide containing products can not be tested by ELISA.

The egg white is processed separately for preparation of biological products that can be used in humans and animals.

The shell membrane is separated from the egg shell and is used for different formulations of biological products for external use in humans and animals. The shell of the hyperimmune egg can be used for preparation of calcium-containing products by drying and granulation. In a second variant, the egg shell and the shell membrane are mixed together generating another product.

IgY Extraction a) Separate the yolk from the white after breaking the vittelin membrane of the eggs collected from immunized hens, 8 or 30 days after the last administration of the given antigen.
b) Measure the volatile of yolk and then mix with cold (+4° C.) distilled water, pH 4.5 at a 1:8 ratio, and blend with a turmix for 2 minutes at room temperature.
c) Adjust the pH to 4.5 and add Thimerosal 0.01% (Thimerosal is not added to some products).
d) Store the mixture for 6 hours or overnight at +4° C.
e) Collect the aqueous phase containing IgY.
f) Extract IgY by filtration at 20° C. using filters that allow the passage of proteins weighing less than 20 kDa to retain the water-insoluble biomolecules, mostly lipids and yolk granules.
g) Store IgY at +4° C. for 7 days or at −22° C. for 6 months. If freeze-dried, it can be stored at least 1 year.

Control Tests for the Ispga Immunogen

The control tests used for the I-spga immunogene are:

1. Microbiological sterility
2. Safety
3. Evaluation of the immune response of the inoculated hens
4. Identification of the G and A biological markers that differentiate these products from the similar ones in Romania or other countries.
5. Evaluation of the immune response of hens against I-spga immunogen as intensity, mg protein/egg, uniformity per immune response in time
6. Evaluation of the complex immune response against *Clostridium difficile* (model and case study)
7. Evaluation of I-spga capacity to transform protein molecules (OTf, OM, OA and LY) into biologically active molecules by ELISA and RSAR 1. Microbiological Sterility The method addresses the testing of the finished product for assessing the presence of microbial or fungal contaminants in the I-spga immunogen solution. The microorganisms may come from the production process or the materials used to prepare the immunogen.

Testing is performed in accordance with provisions of Eurepean Pharmacopoeia 8$^{th}$ edition.

Samples are taken from the finished product vials and inoculated into tryptic soy broth (TSB) and thioglycollate medium (FTM). The samples are incubated at +30-35° C. and +20-25° C., respectively, for a period Of 14 days.

The I-spga immunoglobulin batch is admitted for use if no contaminants are present.

2. Safety of the I-spga Immunogen Administered Intramuscularly to Laying Hens

The safety studies for the I-spga immunogen administered intramuscularly to Rhode Island Red breed laying hens aged 20 weeks consisted of assessment of the reproductive function. Local and general reactions were studied, as well as the influence on the onset of laying and potential adverse effects at all check stages (60-70).

One of the main objectives of these tests was to obtain a prognosis for the effects of the I-Spga immunogen administration in the hens, based on the reactions observed locally, generally and on the laying. The tests were performed to ensure the safety of I-spga immunogen (71). These effects may vary depending on the species and depend on the bioavailability and reactivity of the agent on the receptor called muscle tissue.

Safety Test for I-spga Immunogen
Parameters:
  Reaction at the inoculation site
  General reactions
  Egg production
  Qualify of the eggs
Procedure:
  Laying hens: Rhode Island Red aged 20 weeks
  Number of lots: 2
  Lot 1: I-spga immunogen group where the amount of inoculum is twice as high as the recommended inoculum for intramuscular administration at four different points.
  Lot 2: control group inoculated with 4 ml sterile PBS, 1 ml per each inoculation point
  Number of chickens per group: 10
  Amount of immunogen used in the test: twice the recommended amount.
  Route of administration: intramuscular
  Number of doses: single dose
  If complete or incomplete Freund'S adjuvant is used: NO
  Observation period: 30 days

TABLE 1

Safety assessment of the I-spga immunogen batch 3/2017[a]

| Specification | Local Reaction | General Reaction | Egg Production | Eggs Quality |
|---|---|---|---|---|
| Lot 1 (inoculated with I-spga) | 0/10 | 0/10 | 8% | According to the age |
| Lot 2 (control) | 0/10 | 0/10 | 8.1% | According to the age |

[a]Rhode Island red laying hens, 20 weeks. Number of hens/lot: 10. Amount of I-spga inoculum: 4 ml in 4 different points. Amount of PBS: 2 ml in 4 different points. Number of doses: 1. Observation period: 30 days 3. Evaluation of Immune Response of Hens Immunized with I-spga at 8 Days and 44 Days After First Inoculation To assess the immune response of chickens immunized with I-spga, laboratory techniques are used for the control of precipitins (ELISA, Mancini radial agar immunodifusion test and Ouchterlony double immunodiffusion test) and of agglutinins (rapid serum agglutination test and slow seroagglutination test). For assessment of the direct action of the immune response of the hens against bacterial exotoxins, the in vitro neutralization of exotoxins against Vero and BHK cells is used.

4. Identification of Biological Markers from the I-spga Immunogen

| Specification | Biological Markers[d] | |
|---|---|---|
| | G Marker[a] | A Marker[b] |
| ELISA[c] | present | present |
| Spectophotometric assay | present | ND |

[a]Spectrophotometric detection and ELISA
[b]OD at 1:1000 dilution of IgY
[c]ELISA test using Abcam kits
[d]average of three replicates The markers present in I-spga products prove that the biological products were prepared following the technology described in this patent. At the time of registration of this patent, there is no other biological product containing immunologically active proteins which can be identified by biological markers added for this purpose.

Recommended Models For Use of the Invention

To assess the I-spga immunogens used for hen immunization, it is recommended to control the immune response at 8 days or 44 days after the first inoculation. For this purpose I-spga identification is performed by evaluating the immune response of the hens, in scrum or egg, upon inoculation of the immunogen containing a biological marker (Example No. 1).

For evaluation of the IgY immune response the ELISA test is used.

To evaluate the transformation of the proteins from the egg white, which became immunologically active, the ELISA and the seroagglutination tests are used. These tests are used for assessing the immune response of ovotransferrin, ovomucine, ovalbumin and lysozyme.

Example #1

Identification of I-spga Markers, Which Differentiate These Second-Generation Products from the Related Ones Obtained Previously to this Patent.

Identification of I-spga biological markers is made on egg samples harvested individually or in groups from I-spga immunized hens.

I-spga contains in its components the A and G markers, two proteins that can be confirmed in the laboratory using the ELISA test, the serum agglutination and the agar gel immuno-diffusion.

The G Marker

The G Marker indicates the presence of sodium glutamate in the I-spga biological products. Glutamate (glutamic acid) is one of 20 proteinogenic amino acids. Carboxylated anions and glutamic acid salts are known as glutamates. Glutamate is an important neurotransmitter that plays a key role in potentiating immunologically active proteins in the long run and is important for learning and memory. Glutamic acid is the GABA precursor, but has somewhat the opposite function; it could play a role in the normal functioning of the heart and prostate. As one of the few nutrients that cross the blood-brain barrier, glutamic acid is used in the treatment of some diseases such as depression, ADD and ADHD, fatigue, alcoholism, epilepsy, muscular dystrophy, mental retardation and schizophrenia.

The presence of sodium glutamate in I-spga biological products acts as a potentiator of the immunologically active proteins and as a neurotransmitter.

The detection of sodium glutamate in I-spga biological products is performed by the colorimetric method and the Glutamate Assay Kit (ab83389)/Abcam, 330 Cambridge Science Park, Cambridge CB4 0FL UK. Sodium glutamate is found in the I-spga immunogen, in the immunologically active I-spga products and in the IgY extracted from the yolk of the eggs laid by hens that received the I-spga immunogen (72, 73).

Figure 1:
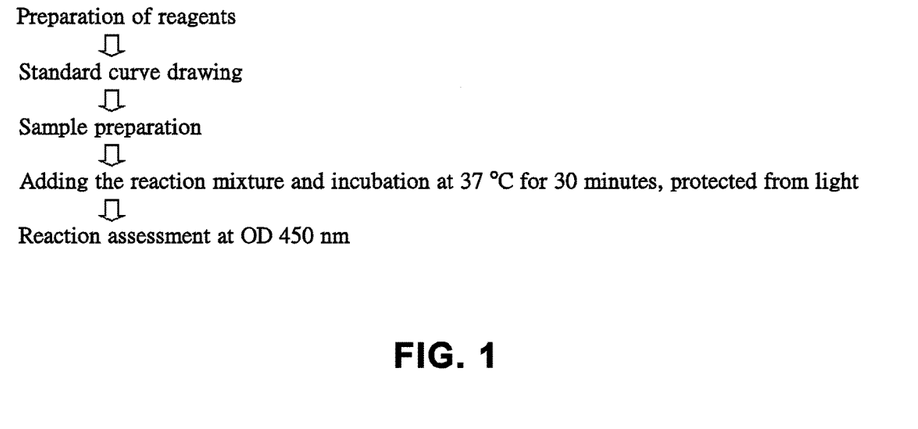
FIG. 1 illustrates the steps of a method for measuring glutamate in different biological samples.

The Glutamate Assay Kit (Fluorometric) (AB138883)/ABcam provides a fast and sensitive method for measuring glutamate (glutamic acid) in different biological samples. In this test, the coupled enzyme system catalyse the reaction between L-glutamic acid and NABF+ to produce NADPH, which is specifically recognized by the NADPH sensor and recycled back to NADP+. During the reaction, a red fluorescence product is generated, which in turn can be detected with a microplate fluorescence reader at Ex/Em=540/590 nm (Ex/Em range=530-570/590-600 nm). This test can detect down to 1 pM glutamic acid. The signal can also Be read By absorbance at OD 576±5 nm, but the sensitivity of the test is reduced by 10 times. The working protocol is shown in FIG. 1.

The A Marker

Figure 2:
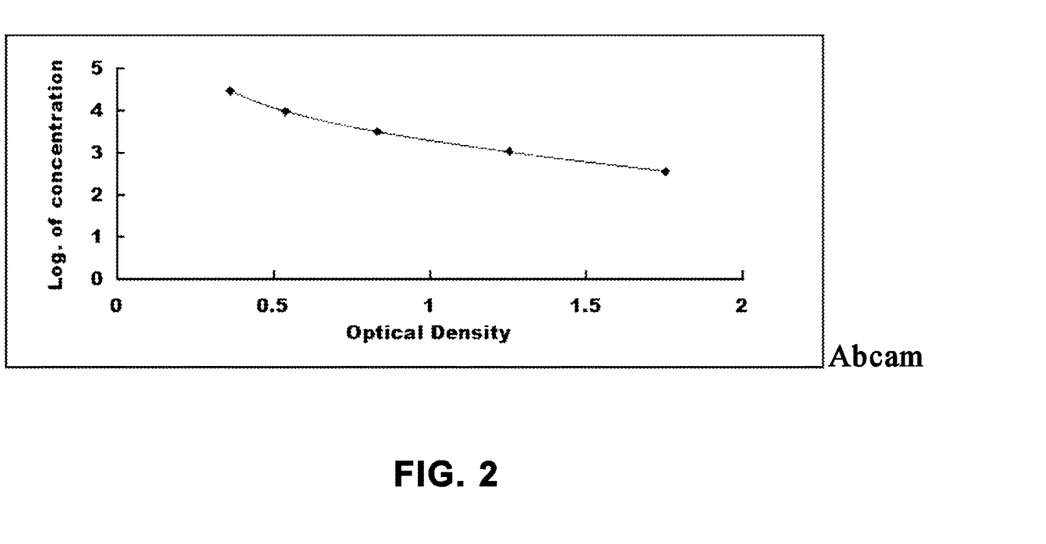
FIG. 2 is the graph of the ELISA identification for A Marker for Bovine Serum Albumin (BSA), catalog number CEA248Ge, Wuhan USCN Business Co., Ltd.
Figure 3:
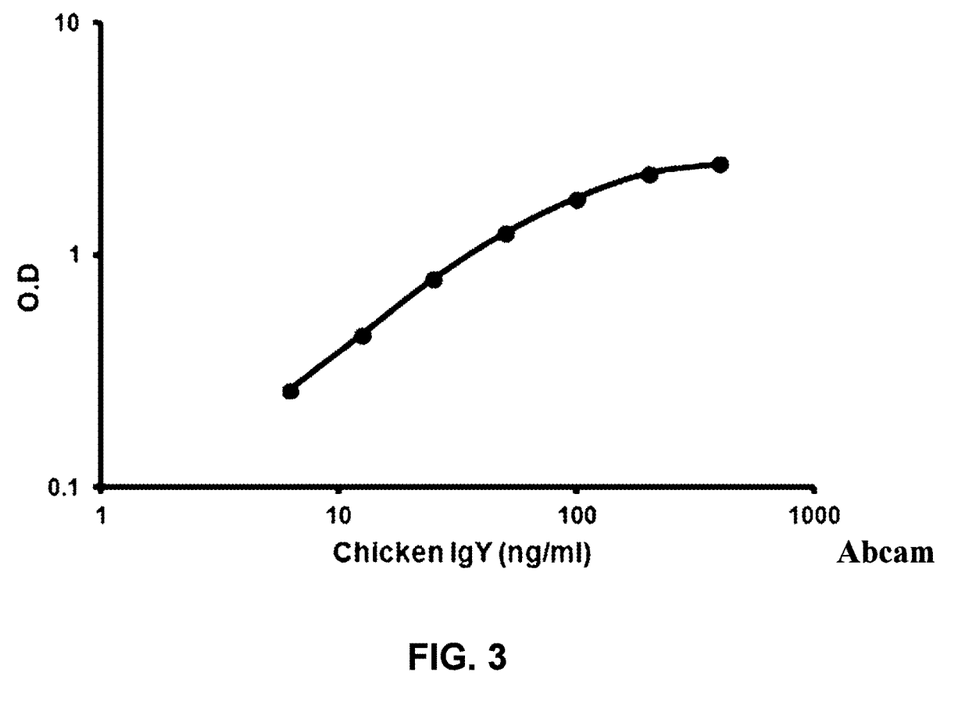
FIG. 3 is the graph for determining the content of IgY in the Imunogall hyperimmune egg assessed using the Abcam methodology and ELISA kit Ab157693.

The A Marker is the bovine albumin used to protect the proteins in liquid medium and lyophilized products. The identification assay for A Marker is ELISA for Bovine Serum Albumin (BSA), catalog number CEA248Ge, Wuhan USCN Business Co., Ltd. See FIG. 2.

BSA is found in the I-spga immunogen, in the immunologically active I-spga biological products, as well as in the IgY extracted from yolk of the eggs laid by hens that received the I-spga immunogen.

Example #2

Determination of the IgY Content in the Hyperimmune Egg

The content if IgY in the Imunogall hyperimmune egg is assessed by using the Abcam methodology and ELISA kit, Ab157693. See FIG. 3.

The IgY content in the Imunogall hyperimmune egg should be 400 ng.

Example #3

Determination of Specific IgY Content by ELISA

The specific activity of IgY is determined qualitatively against the antigen or antigens used for immunization. Strips of different antigens from the I-spga immunogen are attached to the reaction plates and the specific IgY is tested in successive dilutions from 1:100 to 1:1000, respectively, in triplicate. The maximum positive dilution is considered dilution at which the reaction is equal to or greater than 0.200 OD or the mathematical value for dilution greater than 0.200 OD. At this dilution the positive reaction is produced by 5-10 ng of specific IgY per well (150 µl).

Procedure:

a) Coat an ELISA plate with 150 µl of the desired antigen, lyophilized suspension at 1.67-1.70 µg per ml or 10 µg protein per ml in carbonate-bicarbonate buffer (0.05 M, pH 9.6);
b) The coated plate is stored for 12 hours (overnight) at +4° C.;
c) Discard the liquid and wash the plate 3 times with the PBS-Tween 20 wash solution (2%);
d) Block the reaction with 300 µl/well blocking buffer, and incubate 30 minutes at room temperature;
e) Discard the blocking fluid;
f) Dry the plate for 30 minutes in a desiccator;
g) Dispense 100 µl of 1:100 and 1:1000 diluted IgY suspension according to the plate configuration into each well. IgY Under evaluation will be tested in triplicate;
h) Keep wells A1, H1 and H2 as antigen controls, wells B1, C1 and D1 as negative reaction controls using IgY-SPF and wells E1, F1 and G1 as positive controls;
i) Incubate the plate 2 hours at +37° C.;
j) Wash 3 times with washing solution;
k) Add 100 µl of 1:5000 diluted anti-bird IgG conjugate, using the dilution buffer as diluent;
l) Incubate the plate 2 hours at +37° C.;
m) Wash plate 4 times with washing solution;
n) Add 100 µl TMB and leave at room temperature for 5-15 min.
o) Add 100 µl stop solution;
p) Read the reaction on a spectrophotometer at 450 nm.
q) The test is validated when the reactions in the blank wells A1, H1 and H2 are less than 0.060 OD, when the reactions in the B1, C1 and D2 wells with IgG-SPF negative control show values of 0.060-0.090 OD, and the positive control wells E1, F1, G1 exhibit values of 1,400-1,800 OD. The positive reaction of this control test proves that the immunogen produced an adequate and specific immune response.

Example #4

Determination of IgY Content Using the Mancini Simple Radial Immunodiffusion Test.

Simple Radial Immunodeficiency (SRID) was accepted as an accurate test of quantifying an antigen and/or serum antibodies using a standard reagent (27, 28). Using SRID, it is possible to determine with great accuracy the protein content of IgY against anti-IgY rabbit IgG. For this purpose it is recommended to prepare the gel from gelose or agar and to carry the test out by the following steps:

a) Preparation of 1% agarose in PBSA containing 0.05% sodium azide: agarose is heated to 80-90° C. and let to cool to 45-50° C.; serum containing IgG anti-IgY is added at a rate of 0.33 ml/ml of agarose. Keep one milliliter of agarose at 45-50° C.
b) Pour agarose into a disposable plate 4 ml/6 cm diameter and let it cool to room temperature.
c) Punch wells of 6 mm diameter at distances of at least 20 mm, and dispense 0.30 ml warm agar to each well to seal the bottom of the well and not allowing the liquid to pass under the agar. Cool the agar plate to room temperature.
d) Dispense 30 µl of whole IgY and in 1/1, 1/2, 1/4, 1/8 successive dilutions in PBS into the wells.
e) Store the reaction plates at room temperature in a humid environment and read the reaction at 24, 48 and 72 hours.

If necessary, consider to color the agar with Coomassie blue. Fix the gel with methanol containing 10% acetic acid for 30 minutes at room temperature. Remove the fixing solution. Color the gel with 10 volumes of Coommassie Blue dye for one hour or overnight at room temperature (the dye solution may be re-used). Discolor the gel in 10 volumes of decolorant at room temperature for 30 minutes, repeat the discoloration, and soften the gel for 15 minutes in 1-2% glycerol in deionized water. The gel is photographed and the diameter of each precipitation circle is measured. The concentration in milligrams of protein of IgY is assessed either by reference to a reference table or to a standard control.

Example #5

Determination of IgY Content Using the Oucherlony Double Immunodiffusion Test

The ID assay was performed following the Abcam protocol and is based on the migration in the agar gel of the IgY antigen and the antibodies (anti-IgY rabbit serum HAPL 97136 Abcam) which, at the site of contact, combine specifically and form a precipitation line. All tests performed using the AGID technique aimed to identify IgY against international standards. These tests are part of the first category of controls that have been used to identify IgY molecules. The test is valid when the control sample precipitation line joins the standard IgY precipitation line and does not react with the negative control.

Example #6

Assessing the Immune Response 8 Days After Immunization
Control of immunologically active proteins extracted from the I-spga hyperimune egg.

| Specification[c] | IgY[a] | OTf[b] |
|---|---|---|
| IgY | ++++ | — |
| Ovotransfferin | — | ++++ |

[a]Chicken IgY ELISA Kit (ab189577)
[b]Chicken Ovotransferrin ELISA Kit (ab157694)
[c]Tests performed according to Abcam instructions
[d]For each sample three replicates were considered Example #7

Immune Response of Hens Immunized with I-spga Immunogen

To control the immune response of laying hens immunized with the I-spga immunogen, the qualitative ELISA immunoassay was used. For testing the specificity of the antibodies present in the I-spga hyperimun egg, IgY was extracted from the yolk and used for evaluation. A positive reaction (3,000-3,200 OD) was recorded for each specific antibody within the composition of the I-spga polyvalent IgY.

Example #8

Admissibility Conditions

Specimens obtained from the egg of hens hyperimmunized with I-spga must be tested by ELISA, Abcam's or in-house prepared. Tests can be done 8 days or 58 days after first inoculation. IgY I-spga must contain the G and A markers that confirm the manufacturing technology and origin of the product.

IgY I-spga must contain antibodies that respond specifically to each antigen with which the hen has been immunized. In quantitative ELISA test, at 1:1000 IgY dilution, the optimal accepted response for each antibody is 3,000-3,200 OD. This uniform and equal response for each antigen is characteristic for the hen (*Gallus domesticus*).

The invention claimed is:
1. A method of preparing a complex immunogen, the method comprising:
   a) preparing microbial antigens comprising a complex bacterial mixture of 18 to 26 species of pathogenic bacteria, isolated from different patients and consisting of 7 different strains from each species comprising: *Staphylococcus aureus, Staphylococcus epidermidis, Streptococcus pneumoniae, Streptococcus mutans, Streptococcus agalactiae, Streptococcus pyogenes, Enterococcus faecium, Enterococcus faecalis, Neisseria meningitidis, Neisseria Gonorrhoeae, Haemophilus influenzae, Escherichia coli, Klebsiella pneumoniae, Salmonella* spp, *Shigella* spp, *Campylobacter jejuni, Helicobacter pylori, Proteus* spp, *Acinetobacter baumani, Pseudomonas aeruginosa, Fusobacterium nucleatum, Clostridium difficile* comprising a whole-cell bacteria and other bacterial constituents comprising cilia, yeast comprising *Candida albicans, Candida parapsilosis, Candida krusei, Candida qlabrata,* viruses, fungi, exotoxins, endotoxins or spores;
   b) inactivating antigen with a standard immunogen comprising binary ethyleneimine (BEI) or formol;
   c) preparing said complex concoction of immunogen (Immunogen-SPGA, I-SPGA) by supplementing a mixture consisting of 0.218 M (molar) sucrose, 0.0038 M monopotassium phosphate, 0.0072 M dipotassium phosphate, 0.0049 M monosodium glutamate, 1% bovine albumin and an adjuvant comprising Quillaja *Saponaria* (QS21);
   d) parenterally inoculating chickens with the complex concoction of immunogen (Immunogen-SPGA, I-SPGA) disclosed in step c) using 0, 30 and 44 days intervals to produce immunologically active eggs;
   e) extracting immunologically active proteins of an avian origin from said immunologically active eggs and consuming said immunologically active eggs as food supplements.

2. The method of claim 1 further comprises:
   administering an additional antigenic mixture such that the standard immunogen becomes a specific immunogen wherein said additional antigenic mixture is prepared from 6-8 pathogenic strains from a single species of bacteria, fungi or yeasts isolated from patients with endemic infections within a particular or endemic geographical area; and
   reimmunizing said previously inoculated chickens with said specific immunogen in two steps: on day 30 and on day 44 after receiving said complex concoction disclosed in step c) in claim 1.

3. The method claim 1 further comprises:
   preparing a personalized immunogen when an antigenic component of the standard immunogen is prepared from a pathogenic strain derived directly from a pathological material of a patient such that the standard immunogen becomes a customized immunogen for said patient;
   reimmunizing said previously inoculated chickens with said customized immunogen in two steps: on day 30 and on day 44 after receiving said complex concoction disclosed in step c) in claim 1;
   characterized in that the standard immunogen becomes a personalized immunogen by adding a specific pathogenic strain derived directly from the patient's pathological material; hens previously immunized with the standard immunogen are reimmunized with this complex concoction, it in two steps: on day 30 and on day 44, respectively.

4. The method of claim 1, wherein said complex immunogen is immunologically active proteins of avian origin comprising immunoglobulin Y, apo-ovotransferrin, holo-ovotransferrin, ovomucin, ovalbumin and lysozyme and have specific activity to said each species from the source antigen.

5. The method of claim 1, wherein said complex immunogen is immunologically active proteins of avian origin and are contained in a white, a yolk, a vitelline, shell membranes or egg shell, and are used as they are to treat immune deficiencies comprising: bullous epidermolysis, vulgar psoriasis, cytostatic post-treatment immune deficiency.

6. The method of claim 1, wherein said complex immunogen is immunologically active proteins of avian origin and are contained in a white, a yolk, a vitelline, shell membranes, or an egg shell, and are used as they are to treat *Staphylococcus aureus* MSSA and MRSA infections.

7. The method of claim 1, wherein said complex immunogen is immunologically active proteins of avian origin and are contained in a white, a yolk, a vitelline, shell membranes, or an egg shell, and are used as they are to treat nosocomial infections with *Clostridium difficile*.

8. The method of claim 1, wherein said complex immunogen is immunologically active proteins of avian origin and are contained in a white, a yolk, a vitelline, shell membranes, and an egg shell, and are used as they are to treat urinary infections in children and adults.

9. The method of claim 1, wherein said complex immunogen is immunologically active proteins of avian origin and are contained in a white, a yolk, a vitelline, shell membranes, and an egg shell, and are used as they are to treat digestive and/or other organs and tissues infections with sensitive or antibiotic resistant germs.

10. The method of claim 1, wherein said complex immunogen is immunologically active proteins of avian origin and are contained in a white, a yolk, a vitelline, shell membranes, or an egg shell, and are used as they are to treat infectious dermatitis.

11. The method of claim 1, wherein a therapeutic value of said complex immunogen comprising immunologically active proteins of avian origin is increased by including isolated pathogens from patients within a certain geographical area, in the composition of any of the immunogens.

\* \* \* \* \*